US005760283A

United States Patent [19]

Roof et al.

[11] Patent Number: 5,760,283
[45] Date of Patent: Jun. 2, 1998

[54] ACROLEIN SCAVENGERS

[75] Inventors: Glenn L. Roof, Sugarland; Dwight Reid, Houston, both of Tex.

[73] Assignee: Baker Hughes Incorporated, Houston, Tex.

[21] Appl. No.: 745,529

[22] Filed: Nov. 12, 1996

Related U.S. Application Data

[62] Division of Ser. No. 370,668, Jan. 10, 1995, Pat. No. 5,606,094.

[51] Int. Cl.$^6$ .................................................. C07C 255/08
[52] U.S. Cl. ........................................... 558/463; 568/492
[58] Field of Search .............................. 568/492; 558/463

[56] References Cited

U.S. PATENT DOCUMENTS

| | | | |
|---|---|---|---|
| 3,462,477 | 8/1969 | Caporali et al. | 203/DIG. 3 |
| 3,725,208 | 4/1973 | Maezawa et al. | 203/8 |
| 3,893,895 | 7/1975 | Dehnert et al. | 203/59 |
| 3,909,408 | 9/1975 | Ishida et al. | 210/59 |
| 3,923,648 | 12/1975 | Lashley et al. | 210/12 |
| 4,892,719 | 1/1990 | Gesser | 423/245.1 |

FOREIGN PATENT DOCUMENTS

| | | |
|---|---|---|
| 0110861 | 6/1984 | European Pat. Off. |
| 1431511 | 4/1976 | United Kingdom. |
| 2114118 | 8/1983 | United Kingdom. |

OTHER PUBLICATIONS

*Chemical Abstracts* 70:37240z (1969).
*Chemical Abstracts* 75:151381z (1971).
*Chemical Abstracts* 92:129606f (1980).
*Chemical Abstracts* 97:183024f (1982).
Angus Material Safety Data Sheet on Amine CS–1135® (month and year not available).
Angus Chemical Company Technical Data Sheet on Oxaxolidine Chemistry and Uses, (month and year not available).

*Primary Examiner*—Johann Richter
*Assistant Examiner*—Laura L. Stockton
*Attorney, Agent, or Firm*—Rosenblatt & Redano, P.C.

[57] ABSTRACT

A process for removing acrolein from a gaseous or liquid mixture, in one case aqueous solutions, involving contacting the mixture with a compound selected from the group consisting of sodium hypochlorite; an acid salt of hydroxylamine; a urea compound such as urea itself or thiourea; sodium bisulfite and 4,4-dimethyl-1-oxa-3-azacyclopentane in an amount effective to substantially remove acrolein has been discovered. The process works particularly well in selectively scavenging acrolein from aqueous solutions containing acrylonitrile.

12 Claims, No Drawings

ACROLEIN SCAVENGERS

This application is a divisional of application Ser. No. 08/370,668 filed on Jan. 10, 1995, now U.S. Pat. No. 5,606,094.

FIELD OF THE INVENTION

The invention relates to methods for removing acrolein from a gaseous or liquid mixture by reaction with a chemical scavenger, and more particularly relates to removing acrolein from gaseous or liquid mixtures also containing acrylonitrile where the acrolein is selectively removed and removing essentially none of the acrylonitrile.

BACKGROUND OF THE INVENTION

Acrolein is a material known to have toxic effects. Contact with acrolein is preferably avoided or minimized It would be desirable if a method could be discovered which would remove acrolein from mixtures of other valuable materials in a selective fashion while removing essentially none of the other compound or compounds. For example, it is known to separate acrolein from acrylonitrile using extractive distillation with water. However, this technique will not work to extract acrolein from an aqueous solution of acrylonitrile when it is desirable to keep the acrylonitrile in the aqueous solution. The presence of acrolein in acrylonitrile solutions also results in the presence of an acrolein/cyanohydrin adduct, which is also to be avoided Some methods of removing acrolein from waste gas include, but are not necessarily limited to, the use of membrane separation, catalytic oxidation, activated carbon, and silica gel containing an iron phthalocyanine catalyst. Catalytic oxidation and distillation at certain pH levels have also been used to remove acrolein from acrylonitrile. Other processes for removing acrolein from acrylonitrile include ion exchange resins and condensation, the latter procedure which has also been used to remove acrolein from acrylic acid. However, there remains a need for acrolein scavengers that can selectively react with acrolein relative to the other species in the solution.

SUMMARY OF THE INVENTION

Accordingly, it is an object of the present invention to provide a method for selectively removing acrolein from gaseous arid/or liquid mixtures.

It is another object of the present invention to provide a method for selective acrolein removal from gaseous and/or liquid mixtures which does not require a complex series of specialized steps.

A further object of the invention is to provide a technique of selectively removing acrolein from gaseous and/or liquid mixtures using readily available materials as scavengers.

In carrying out these and other objects of the invention, there is provided, in one form, a process for removing soluble acrolein from gaseous and/or liquid mixtures comprising contacting the mixture with a compound selected from the group consisting of sodium hypochlorite; an acid salt of hydroxylamine; urea compounds, such as urea itself and thiourea; sodium bisulfite and an oxazolidine known as 4,4-dimethyl-1-oxa-3-azacyclopentane; in an amount effective to substantially remove acrolein.

DETAILED DESCRIPTION OF THE INVENTION

It has been discovered that certain compounds are useful in the selective scavenging of acrolein. For example, sodium hypochlorite (NaOCl), a common compound for household bleach; along with certain nitrogen-containing compounds, specifically hydroxylamine ($H_2N$—OH); urea compounds, including, but not necessarily limited to urea itself ($H_2N$—(C=O)—$NH_2$) and thiourea ($H_2N$—(C=S)—$NH_2$); and sodium bisulfite ($NaHSO_3$) have all been found to selectively remove acrolein from gaseous and/or liquid mixtures, in one embodiment, preferably aqueous solutions. Preferably, hydroxylamine is used in the form of an acid salt, including, but not necessarily limited to hydroxylamine hydrochloride, hydroxylamine sulfate, hydroxylamine acetate, and other inorganic and organic acid salts. Additionally, 4,4-dimethyl-1-oxa-3-azacyclopentane, an oxazolidine having the formula:

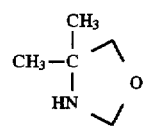

was also discovered to be an effective acrolein scavenger. This oxazolidine is made from the reaction of one mole of 2-hydroxymethyl-2-propanamine with one mole of formaldehyde and is available from Angus Chemical as Amine CS-1135® oxazolidine.

The proportions or amounts of the various scavengers effective to substantially remove acrolein range are noted in Table I where the wt. % is based on the total aqueous solution.

TABLE I

Effective Proportions of Acrolein Scavengers

| Scavenger | Broad Range | Preferred Range |
|---|---|---|
| sodium hypochlorite | 10 ppm to 20 wt. % | 500 ppm to 5 wt. % |
| hydroxylamine acid salt | 10 ppm to 20 wt. % | 500 ppm to 5 wt. % |
| urea compounds | 10 ppm to 20 wt. % | 500 ppm to 5 wt. % |
| 4,4-dimethyl-1-oxa-3-azacyclo-pentane | 10 ppm to 20 wt. % | 1000 ppm to 10 wt. % |
| sodium bisulfite | 10 ppm to 20 wt. % | 500 ppm to 5 wt. % |

By removal of a substantial amount of acrolein is meant at least 80% wt. % of the acrolein initially present, preferably at least 85 wt. % of the acrolein is removed. Conversely, when a valuable compound is present in the gaseous and/or aqueous mixture, for example, acrylonitrile; it is preferred that essentially all of this other compound remain in the mixture. It will be understood that in some embodiments, the gas or liquid stream to be treated may contain only acrolein and one other compound. For example, some acrylonitrile product streams may contain only a mixture of acrylonitrile and acrolein. Such streams are not aqueous solutions for no water is included. Nevertheless, the method of the invention is anticipated to be useful for such streams as well.

The process of the invention is practiced simply by adding an effective amount of the scavenger to the gaseous and/or liquid mixtures to substantially remove the acrolein. To improve reaction of the scavenger with acrolein, the scavenger should be intimately mixed with the aqueous solution by shaking or stirring, in the case of batch processes, or by static in-line mixers, baffles or other such means for continuous processes. It is expected that the process of this invention would work in a temperature range of from about 25° to about 127° C. The removal of the reaction products of the scavenger and acrolein may be accomplished by any technique known in the art, including, but not limited to, distillation. It is anticipated that the reaction products of the scavengers herein with acrolein would be relatively higher boiling materials, since some of them would have roughly twice the molecular weight of acrolein; others, such as acrylic acid, would be rendered much higher boiling than acrolein due to increased polarity. Thus, upon distillation of the desired acrylonitrile (or other material), the reaction products of acrolein and the scavenger would accumulate in the bottoms and eventually be part of a wastewater stream.

Experimental Procedure A

The procedure used to screen candidates for the process of this invention is as follows:

1. Prepare a standard solution containing 1.00% of both acrolein and acrylonitrile (AN) in $H_2O$.

2. Pre-dose a 1 oz. bottle with excess candidate (with the exception of NaOCl, bleach).

3. Add 1.00 ml of standard solution from above to each bottle, including a blank.

4. Shake all samples including the 1.00 ml of standard/blank overnight on a wrist-action shaker.

5. Inject about 1 µl of the blank and each sample on a gas chromatograph and run isothermally at 35° C. using a 30 m Megabore DB-5 column with flame ionization detection (FID). Acrolein elutes at about 5 minutes and AN at about 6 minutes. Injector and detector temperatures should be 120° and 250° C., respectively.

6. Calculate % acrolein (Acr.) and % AN remaining using the following formulae:

$$\% \text{ Acr. remaining} = \frac{\text{Area Counts of Acrolein}_{sample}}{\text{Area Counts of Acrolein}_{std}} \times$$

$$100 \times \frac{\mu l \text{ std injected}}{\mu l \text{ sample injected}}$$

$$\% \text{ AN remaining} = \frac{\text{Area Counts of AN}_{sample}}{\text{Area Counts of AN}_{std}} \times$$

$$100 \times \frac{\mu l \text{ std injected}}{\mu l \text{ sample injected}}$$

Multiple standard injections were made and the area counts of each component per µl injected were somewhat variable; consequently, the standard/blank area counts used in the calculations always correspond to the most recent standard injection. The results are shown in Tables II and III. It is noted that the amount of blank used in all Examples was 1.00 ml (1% in both acrolein and acrylonitrile).

TABLE II

Screening for Acrolein Scavengers

| | | | | Analysis | |
|---|---|---|---|---|---|
| Ex | Candidate | Dose | Amount | % Acrolein remaining | % AN[1] remaining |
| 1 | Commercial bleach (3.62% NaOCl) | 9.1%* | 100 µl | 2 | 98 |
| 2 | Commercial bleach (3.62% NaOCl) | 9.1%* | 100 µl | 7 | 100 |
| 3 | (HO—$NH_3$)$_2{}^+SO_4{}^-$ | 4.8% | 50 mg | 3 | 74 |
| 4 | $NaNO_2$ | 5.9% | 63 mg | 38 | 100 |
| 5 | $NaNO_2$ | 5.9% | 63 mg | 23 | 100 |
| 6 | $NaNO_2$ | 5.9% | 63 mg | 29 | 100 |
| 7 | $NaNO_2$ | 5.9% | 63 mg | 23 | 100 |
| 8 | Thiourea | 5.3% | 56 mg | 16 | 100 |

TABLE II-continued

Screening for Acrolein Scavengers

| | | | | Analysis | |
|---|---|---|---|---|---|
| Ex | Candidate | Dose | Amount | % Acrolein remaining | % AN[1] remaining |
| 9 | Thiourea | 5.3% | 56 mg | 28 | 100 |
| 10 | Ethanolamine | 4.8%* | 50 µl | 50 | 9 |
| 11 | Hydrazine | 4.8%* | 50 µl | 4 | 0 |
| 12 | Hydrazine | 4.8%* | 50 µl | 7 | 0.5 |
| 13 | oxazolidine (50% dilution of CS-1135 ®) | 9.1%* | 100 µl | 0 | 67 |
| 14 | oxazolidine (50% dilution of CS-1135 ®) | 9.1%* | 100 µl | 11 | 63 |
| 15 | Morpholine | 4.8%* | 50 µl | 55 | 0.2 |
| 16 | $NaNO_2$ | 4.7% | 49 mg | 36 | 32 |
| 17 | $NaNO_2$ | 4.7% | 49 mg | 18 | 39 |
| 18 | $NaHSO_3$ | 5.9% | 63 mg | 59 | 100 |
| 19 | $NaHSO_3$ | 5.9% | 63 mg | 149 | 93 |
| 20 | Fresh 30% $H_2O_2$ | 9.1%* | 100 µl | 37 | 83 |
| 21 | Fresh 30% $H_2O_2$ | 9.1%* | 100 µl | 39 | 88 |
| 22 | 30% $H_2O_2$ | 9.1%* | 100 µl | 46 | 100 |
| 23 | 30% $H_2O_2$ | 9.1%* | 100 µl | 100 | 100 |
| 24 | $NaHSO_3$ | 5.3% | 56 mg | 52 | 60 |
| 25 | $NaHSO_3$ | 5.3% | 56 mg | 41 | 40 |
| 26 | 70% aqueous soln. t-butyl hydroperoxide | 9.1%* | 100 µl | 76 | 100 |
| 27 | 70% aqueous soln. t-butyl hydroperoxide | 9.1%* | 100 µl | 76 | 100 |

[1]In cases where the actual % AN exceeded 100, the % acrolein was normalized to 100% AN.
*Volume %.

TABLE III

Screening for Acrolein Scavengers
Note: Amount of blank used in all Examples was
1.00 ml (1% in both acrolein and acrylonitrile).

| | | | | Analysis | |
|---|---|---|---|---|---|
| Ex | Candidate | Dose | Amount | % Acrolein remaining | % AN[1] remaining |
| 28 | Commercial bleach (3.62% NaOCl) | 9.1%* | 100 µl | 18 | 100 |
| 29 | Commercial bleach (3.62% NaOCl) | 9.1%* | 100 µl | 34 | 100 |
| 30 | (HO—$NH_3$)$^{+Cl-}$ | 4.8% | 50 mg | 72 | 100 |
| 31 | (HO—$NH_3$)$^{+Cl-}$ | 4.8% | 50 mg | 3 | 100 |
| 32 | (HO—$NH_3$)$^{+Cl-}$ | 4.8% | 50 mg | 6 | 100 |
| 33 | $NaNO_2$ | 5.7% | 61 mg | 59 | 100 |
| 34 | $NaNO_2$ | 5.7% | 61 mg | 13 | 100 |
| 35 | 30% $H_2O_2$ | 9.1%* | 100 µl | 93 | 100 |
| 36 | 30% $H_2O_2$ | 9.1%* | 100 µl | 63 | 100 |
| 37 | 70% t-butyl hydroperoxide | 9.1%* | 100 µl | —† | — |
| 38 | 70% t-butyl hydroperoxide | 9.1%* | 100 µl | —† | — |

[1]In cases where the actual % AN exceeded 100, the % acrolein was normalized to 100% AN.
*Vol. %
†Interfering peaks prevented observation of the acrolein peak.

It may be seen from Table II that sodium hypochlorite (bleach) (Examples 1, 2, 28, 29), hydroxylamine (Examples 3, 31, 32), thiourea (Examples 8, 9) and the 4,4-dimethyl-1-oxa-3-azacyclopentane (Examples 13, 14) are suitable acrolein scavengers. Example 30 is believed to be an erroneous data set in light of Examples 3, 31 and 32. Monoethanolamine, hydrazine and morpholine are unacceptable since they consume acrylonitrile faster than acrolein. Others are not selective enough. For example, hydrogen peroxide ($H_2O_2$; Examples 20–23, 35, 36) and sodium nitrite ($NaNO_2$; Examples 4, 5, 16, 17, 33, 34)

scavenge acrolein, but also may consume acrylonitrile to an undesirable extent. It may be seen that 40% t-butyl hydroperoxide (Examples 26, 27, 37, 38) also do not work. It is further noted that in Examples 18, 19, 24, 25, sodium bisulfite (NaHSO$_3$) did not perform as well as hoped; it is believed that this is because the injector temperature for step 5 of these Examples was 200° C. and the higher temperature caused the acrolein to be released from the reaction product of acrolein and sodium bisulfite, although the inventors do not want to be limited by any particular theory. In any event, when the injector temperature was lowered to 120° C. as in Example 49, below, sodium bisulfite was found to be an effective scavenger.

In one battery of testing where Experimental Procedure A was modified by using samples with 100 ppm acrolein, only hydroxylamine was found to be a good performer out of a total of four possibilities. However, it is believed that the poor performance of the candidates was due to an inadequate experimental procedure for testing at the lower concentration of 100 ppm acrolein at ambient temperature. It is believed that eventually a good procedure will be developed for testing at these levels.

Table IV presents additional data for six candidates, conducted according to Experimental Procedure A. Note that urea in Example 44 shows some ability to scavenge acrolein, although it does not appear to be as effective as thiourea.

TABLE IV

Screening for Acrolein Scavengers
Note: Amount of blank used in all Examples was
1.00 ml (1% in both acrolein and acrylonitrile).

| | | | Analysis | |
|---|---|---|---|---|
| Ex Candidate | Dose | Amount | % Acrolein[1] remaining | % AN remaining |
| 39 Commercial bleach (3.62% NaOCl) | 10% | 100 µl | 29 (28) | 104 |
| 40 (HO—NH$_3$)$_2$$^+$SO$_4$$^-$ | 5.2% | 52 mg | 0.15 | 100 |
| 41 50% CS-1135 ® | 10% | 100 µl | 5 | 84 |
| 42 10% Zolidine ® ZT-55 | 50% | 500 µl | 105 (92) | 114 |
| 43 Thiourea | 5.6% | 56 mg | 12 (8) | 151 |
| 44 Urea | 5.0% | 50 mg | 51 (42) | 122 |

[1]In all cases where the actual % acrylonitrile (AN) exceeded 100, the % acrolein data was normalized to 100% AN, where the normalized data is shown in parentheses..

The Zolidine® ZT-55 oxazolidine from Angus Chemical Company is 5-hydroxymethyl-1-aza-3,7-dioxabicyclo [3.3.0] octane of the structure:

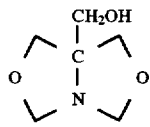

As can be seen from Example 42, it did not perform very well.

Using Experimental Procedure B set out below, sodium hypochlorite (bleach); hydroxylamine sulfate; 4,4-dimethyl-1-oxa-3-azacyclopentane; thiourea and sodium bisulfite were tested in an aqueous solution of 150 ppm acrolein and 225 ppm acrylonitrile (AN).

Experimental Procedure B

The procedure used to screen candidates for the process of this invention using more dilute solutions of acrolein is as follows:

1. Prepare a solution containing 150 ppm acrolein and 225 ppm acrylonitrile (AN) in H$_2$O.

2. Dose a ½ oz. bottle with approximately a ten-fold excess of each candidate.

3. Add 1.00 ml of the untreated solution from step 1 to each bottle, including a blank.

4. Cap bottles and shake 50 times, then place in oven at 90° C. for 1 hour. After one-half hour, shake the bottles 50 times again.

5. Allow samples to cool to room temperature.

6. Inject 1.0 µl of the blank and each sample on a gas chromatograph and run isothermally at 35° C. using a 30 m Megabore DB-5 column with flame ionization detection (FID). Acrolein elutes at about 5 minutes and AN at about 6 minutes. Injector and detector temperatures should be 120° and 250° C., respectively.

7. Calculate % acrolein and % AN as in step 6 of Experimental Procedure A.

TABLE V

Screening for Acrolein Scavengers
Note: Amount of blank used in all Examples was 1.00 ml
(150 ppm acrolein and 225 ppm acrylonitrile).

| | | | Analysis | |
|---|---|---|---|---|
| Ex Candidate | Dose | Amount | % Acrolein remaining | % AN remaining |
| 45 Commercial bleach (3.62% NaOCl) | 3.5% | 36 mg | 73 | 92 |
| 46 (HO—NH$_3$)$_2$$^+$SO$_4$$^-$ | 2000 ppm | 2.0 mg | 0 | 89 |
| 47 50% CS-1135 ® | 4,300 ppm | 4.3 mg | 0 | 53 |
| 48 Thiourea | 1,600 ppm | 1.6 mg | 93 | 93 |
| 49 NaHSO$_3$ | 1,700 ppm | 1.7 mg | 0 | 81 |

Examples 46, 47 and 49 show that hydroxylamine sulfate; 4,4-dimethyl-1-oxa-3-azacyclopentane and sodium bisulfite, respectively, scavenge all of the acrolein; however, it appears possible that they are also reacting with the acronitrile to some extent. Also, bleach and thiourea do not appear to do a good job of scavenging acrolein under these conditions. However, it will be appreciated that the screening methodology for these much more dilute solutions of acrolein have not been perfected and need further refinement.

Many modifications may be made in the present invention without departing from the spirit and scope thereof which are defined only by the appended claims. For example, a routineer in the art may discover that a particular scavenger works particularly well, e.g. especially selectively, when removing acrolein from an aqueous solution containing certain compounds that desirably remain in the solution.

We claim:

1. A process for removing acrolein from a gaseous or liquid mixture comprising contacting the mixture with a compound selected from the group consisting of sodium hypochlorite, an acid salt of hydroxylamine, a urea compound, and 4,4-dimethyl-1-oxa-3-azacyclopentane in an amount effective to substantially remove acrolein.

2. The process of claim 1 where the amounts of the compound effective to substantially remove acrolein ranges from about 10 ppm to about 20 wt. % based on the total mixture.

3. A process for removing acrolein from a gaseous or liquid mixture containing acrylonitrile comprising:

(1) contacting the mixture with from about 10 ppm to about 20 wt. %, based on the total mixture of a compound selected from the group consisting of sodium hypochlorite; an acid salt of hydroxylamine; a urea compound; and 4,4-dimethyl-1-oxa-3-azacyclopentane; and (2) selectively removing substantially all of the acrolein.

4. A process for removing acrolein from a gaseous or liquid mixture comprising contacting the mixture with an acid salt of hydroxylamine in an amount effective to substantially remove acrolein.

5. The process of claim 7 where the an acid salt of hydroxylamine is used in an amount from about 10 ppm to about 20 wt. %, based on the total mixture.

6. A process for removing acrolein from a gaseous or liquid mixture containing acrylonitrile comprising:

(1) contacting the mixture with from about 10 ppm to about 20 wt. %, based on the total mixture, of an acid salt of hydroxylamine selected from the group consisting of hydroxylamine hydrochloride, hydroxylamine sulfate and hydroxylamine acetate; and (2) selectively removing substantially all of the acrolein.

7. A process for removing acrolein from a gaseous or liquid mixture comprising contacting the mixture with a urea compound in an amount effective to substantially remove acrolein.

8. The process of claim 7 where the urea compound is used in an amount from about 10 ppm to about 20 wt. %, based on the total mixture.

9. A process for removing acrolein from a gaseous or liquid mixture containing acrylonitrile comprising:

(1) contacting the mixture with from about 10 ppm to about 20 wt. %, based on the total mixture, of a urea compound selected from the group consisting of urea and thiourea; and (2) selectively removing substantially all of the acrolein.

10. A process for removing acrolein from a gaseous or liquid mixture comprising contacting the mixture with 4,4'-dimethyl-1-oxa-3-azacyclopentane in an amount effective to substantially remove acrolein.

11. The process of claim 10 where the 4,4'-dimethyl-1-oxa-3-azacyclopentane is used in an amount from about 10 ppm to about 20 wt. %, based on the total mixture.

12. A process for removing acrolein from a gaseous or liquid mixture containing acrylonitrile comprising the steps of:

(1) contacting the mixture with from about 10 ppm to about 20 wt. %, based on the total mixture, of 4,4'-dimethyl-1-oxa-3-azacyclopentane; and (2) selectively removing substantially all of the acrolein while removing essentially none of the acrylonitrile.

* * * * *

UNITED STATES PATENT AND TRADEMARK OFFICE
CERTIFICATE OF CORRECTION

PATENT NO. : 5,760,283
DATED : June 2, 1998
INVENTOR(S) : Glen L. Roof, [Dwight Reid], Muslim D. Shahid It is certified that error appears in the above-identified patent and that said Letters Patent is hereby corrected as shown below:

Cover page: please change name of co-inventor "Dwight Reid" to --Muslim D. Shahid --.

Column 1, line 45, please delete the word "arid" and insert therefor the word -- and--.

Signed and Sealed this

Twentieth Day of July, 1999

*Attest:*

*Attesting Officer*

Q. TODD DICKINSON

*Acting Commissioner of Patents and Trademarks*